(12) United States Patent
Fu et al.

(10) Patent No.: US 11,712,447 B2
(45) Date of Patent: Aug. 1, 2023

(54) METHODS OF MANUFACTURING A HIGH MOLECULAR WEIGHT HEPARIN COMPOUND

(71) Applicant: NexEos Diagnostics, Inc., Pottstown, PA (US)

(72) Inventors: Li Fu, Springdale, OH (US); Zhenyu Wang, West Chester, OH (US); Jessica Pax, Cincinnati, OH (US)

(73) Assignee: NexEos Diagnostics, Inc., Pottstown, PA (US)

( * ) Notice: Subject to any disclaimer, the term of this patent is extended or adjusted under 35 U.S.C. 154(b) by 0 days.

(21) Appl. No.: 17/743,154

(22) Filed: May 12, 2022

(65) Prior Publication Data

US 2022/0362283 A1    Nov. 17, 2022

Related U.S. Application Data

(60) Provisional application No. 63/187,624, filed on May 12, 2021.

(51) Int. Cl.
| | | |
|---|---|---|
| *A61K 31/727* | (2006.01) | |
| *A61K 47/02* | (2006.01) | |
| *A61P 7/02* | (2006.01) | |
| *A61K 9/08* | (2006.01) | |

(52) U.S. Cl.
CPC ............. *A61K 31/727* (2013.01); *A61K 9/08* (2013.01); *A61K 47/02* (2013.01); *A61P 7/02* (2018.01)

(58) Field of Classification Search
CPC ............. A61K 31/727; C08B 37/0003; C08B 37/0075
See application file for complete search history.

(56) References Cited

U.S. PATENT DOCUMENTS

| | | | |
|---|---|---|---|
| 4,446,126 A | 5/1984 | Jordan | |
| 4,539,398 A | 9/1985 | Rosenberg | |
| RE35,770 E * | 4/1998 | Lormeau | C08B 37/0066 536/55.1 |
| 6,197,943 B1 | 3/2001 | Casu et al. | |
| 8,003,782 B1 | 8/2011 | Brown et al. | |
| 9,789,212 B2 | 10/2017 | Pease et al. | |
| 2007/0287683 A1* | 12/2007 | Shriver | A61P 37/06 514/56 |
| 2011/0288283 A1* | 11/2011 | Flengsrud | C08B 37/0066 536/55.1 |
| 2013/0150323 A1 | 6/2013 | Parsons et al. | |
| 2015/0057340 A1 | 2/2015 | Thess et al. | |
| 2015/0328159 A1 | 11/2015 | Whitfield et al. | |

FOREIGN PATENT DOCUMENTS

| | | |
|---|---|---|
| BR | 102014027804 A2 | 6/2016 |
| EP | 3943513 A1 | 1/2022 |
| RU | 2606836 C2 | 1/2017 |
| WO | 2021163190 A1 | 8/2021 |

OTHER PUBLICATIONS

Xie, J. et al "Separation of water-soluble polysaccharides . . . " Carbohyd. Polym., vol. 101, pp. 479-483. (Year: 2014).*
Schwartz, L. et al "Introduction to tangential flow filtration . . . " Pall Corporation bulletin, pp. 1-10. (Year: 2014).*
Ashoor et al., "Nebulized heparin and salbutamol versus salbutamol alone in acute exacerbations of chronic obstructive pulmonary disease requiring mechanical ventilation: a double-blind randomized controlled trial," Korean J Anesthesiol, 2020, 73(6):509-517.
Duska et al., "Scintigraphic detection of experimental myocardial infarction with 99mTc-heparin in the dog," Nuklearmedizin, 1985, 24: 111-114.
Esquerré et al., "Kinetics of technetium-labeled heparin in thromboembolism: Preliminary Report," Int J Nucl Med Biol, 1979, 6(4): 215-220.
Hiebert et al., "Tissue distribution and antithrombotic activity of unlabeled or 14C-labeled porcine intestinal mucosal heparin following administration to rats by the oral route," Can J Physiol Pharmacol, 2000, 78: 307-320.
Hiremath et al., "Heparin in the long-term management of ligneous conjunctivitis: a case report and review of literature," Blood Coagul Fibrinolysis, Oct. 2011, 22(7): 606-609.
Hirsh et al., "Heparin and low-molecular-weight heparin: mechanisms of action, pharmacokinetics, dosing, monitoring, efficacy, and safety," Chest, 2001, 119: 64S-94S.
Huber et al., "Cellular and Molecular Effects of High-Molecular-Weight Heparin on Matrix Metalloproteinase 9 Expression," International Journal of Molecular Sciences, 2019, 20(7): 1595.
International Search Report and Written Opinion for PCT/US2021/017453 dated Jun. 25, 2021.
International Search Report and Written Opinion for PCT/US2022/029014 dated Sep. 2, 2022.
Kitschke et al., "Kinetics of [99mTc]heparin, venous scintigraphy with [99mTc]fibrinogen and beta-thromboglobulin assay in the diagnosis of deep-vein thrombosis," Int J Nucl Med Biol, 1984, 11: 235-241.

(Continued)

*Primary Examiner* — Leigh C Maier
(74) *Attorney, Agent, or Firm* — DLA Piper LLP (US)

(57) ABSTRACT

A method of manufacturing a high molecular weight heparin (HMWH) compound is disclosed. The method comprises dissolving heparin to form a heparin solution and fractionating the heparin solution via tangential flow filtration (TFF) using a membrane with a molecular weight cut off (MWCO) between about 8 kDa and about 12 kDa. The TFF yields a retentate comprising fractionated heparin with a weight average molecular weight of about 20 kDa or greater, i.e., a high molecular weight heparin compound. A substantial proportion of heparin chains in the fractionated heparin may have a high molecular weight, e.g., 50% of the heparin chains or greater may have a molecular weight of 20 kDa or greater.

32 Claims, 3 Drawing Sheets

(56) References Cited

OTHER PUBLICATIONS

Kondashevskaya et al., "Effect of single and repeated administration of high-molecular-weight heparin in low doses on brain content of neurotransmitters in Wistar rats," Bulletin of Experimental Biology and Medicine, 2006, 141(5): 599-601.

Kulkarni et al., "Technetium labeled heparin: preliminary report of a new radiopharmaceutical with potential for imaging damaged coronary arteries and myocardium," J Nucl Med, 1978, 19: 810-815.

Kulkarni et al., "Modified technetium-99m heparin for the imaging of acute experimental myocardial infarcts," J Nucl Med, 1980, 21: 117-121.

Laforest et al., "Pharmacokinetics and biodistribution of technetium 99m labelled standard heparin and a low molecular weight heparin (enoxaparin) after intravenous injection in normal volunteers," Br J Haematol, 1991, 77: 201-208.

Majdalani et al., "Kinetics of technetium-labeled heparin in hemodialyzed patients," Kidney Int Supply, 1993, 41: S131-134.

Saffari et al., "Technetium-labeled heparin: A new approach to detection of eosinophilic esophagitis-associated inflammation," J Allergy Clin Immunol, 2013, 1446-1448.

Utne et al., "A gamma camera method for the evaluation of deep-vein thrombosis in the leg. Application of 99mTc-labelled heparin," Eur J Nucl Med, 1981, 6: 237-240.

* cited by examiner

METHODS OF MANUFACTURING A HIGH MOLECULAR WEIGHT HEPARIN COMPOUND

CROSS-REFERENCE TO RELATED APPLICATIONS

This application claims the benefit of priority to U.S. Provisional Application No. 63/187,624 entitled "Methods of Manufacturing a High Molecular Weight Heparin Compound," filed May 12, 2021, which is incorporated herein by reference in its entirety.

SUMMARY

The present disclosure relates generally to methods of manufacturing a high molecular weight heparin compound. The disclosed subject matter may be applied for producing compounds and/or compositions therewith for imaging, diagnosis, monitoring, and/or treatment of various conditions. For example, the compounds produced by the methods disclosed herein may be useful to image, diagnose, monitor, and/or treat eosinophil-related inflammation and eosinophil-related conditions such as eosinophilic esophagitis and eosinophil-associated ocular diseases.

Historically, high molecular weight heparin has been avoided in favor of low molecular weight heparin in the medical field. Heparin is a polysaccharide with an inherent heterogeneity in terms of lengths of polymer chains such that it includes heparin chains of varying molecular weights. Heparin is commonly depolymerized and fractionated to reduce molecular weight, yielding the low molecular weight heparin for administration to patients. It is suspected that administration of significant quantities of high molecular weight heparin chains by the common routes of administration (i.e., intravenously or subcutaneously) increases the incidence of heparin-induced thrombocytopenia (HIT), a complication that results from exposure to heparin and can have limb- and life-threatening thrombotic complications. In HIT, the immune system forms antibodies against heparin when it is bound to platelet factor 4 (PF4). The antibodies then form a complex with the heparin/PF4 and bind and activate platelets, resulting in the formation of blood clots and a drop in platelet count. HIT can lead to venous thromboembolism and in some cases arterial thrombosis (known as HITT). Due to the risk of HIT suspected to be associated with high molecular weight heparin chains, low molecular weight heparin has been favored in the medical field for clinical applications.

However, recent advancements suggest that high molecular weight heparin may provide an advantage in particular applications. For example, high molecular weight heparin may be useful in localizing at high rates to eosinophils, which are a category of white blood cells responsible for combating multicellular parasites and certain infections in vertebrates.

Normally, eosinophils reside in the blood stream, the lower gastrointestinal tract, and the lymphatic system, but infiltrate pathologically into additional organs and regions and can lead to inflammation and a variety of conditions and disorders. A distinctive characteristic of eosinophils is their granules, which comprise markedly cationic proteins. The granule is composed of an electron-dense central core and an electron-radiolucent matrix. The core primarily comprises major basic protein 1 (MBP-1 or eMBP-1); the matrix comprises eosinophil peroxidase (EPO), eosinophil derived neurotoxin (EDN), and the eosinophil cationic protein (ECP). The granule also contains major basic protein 2 (MBP-2 or eMBP-2) in the core and/or the matrix. Upon degranulation, an eosinophil releases each of these proteins into the surrounding tissues, which may stimulate histamine release and cause inflammation among other symptoms. Studies have shown that MBP-1 is toxic to mammalian cells, bacteria and certain forms of parasites, and it was deposited at sites of inflammation in numerous eosinophil-related diseases in association with organ dysfunction (e.g., eosinophilic esophagitis). Heparin is effective in binding to MBP-1 and neutralizing the cytotoxic effects of MBP-1 in a dose related manner. Further, the avidity of heparin to MBP-1 may increase with molecular weight. Accordingly, high molecular weight heparin may be useful for imaging, diagnosing, monitoring, and/or treating eosinophil-related inflammation and/or a host of eosinophil-related conditions.

Despite these advancements, several challenges have hindered the production of high molecular weight heparin. The lack of uniformity in chain length that is inherent to heparin creates major difficulties in isolating chains of a particular molecular weight. Given the focus on low molecular weight heparin in the medical field, methods of producing low molecular weight heparin compounds have been successful. However, there has not been similar progress in developing methods of fractionating high molecular weight heparin.

Further, even where heparin compounds having a targeted average molecular weight (e.g., low molecular weight heparin) have been successfully produced, the molecular weight nonetheless varies greatly such that the compounds may not have a high proportion of heparin chains within the targeted molecular weight range.

Accordingly, it would be advantageous to have a method of manufacturing a high molecular weight heparin compound having a high average molecular weight and a high proportion of the heparin chains having high molecular weight.

Embodiments of the invention are directed to a method of manufacturing fractionated heparin, the method comprising: dissolving heparin in a solvent to form a heparin solution; and fractionating the heparin solution by tangential flow filtration using a fractionation membrane with a molecular weight cut off between about 8 kDa and about 12 kDa, thereby yielding fractionated heparin with an average molecular weight of about 20 kDa or greater, wherein at least 50% of heparin chains in the fractionated heparin have a molecular weight of 20 kDa or greater.

Additional embodiments of the invention are directed to a method of manufacturing a high molecular weight (HMW) heparin, the method comprising: dissolving a heparin salt in a salt solution to form a heparin solution; sterilizing the heparin solution by filtering through a sterilization membrane having a pore size of about 0.2 μm, thereby yielding a sterilized heparin solution; fractionating the sterilized heparin solution by tangential flow filtration using a fractionation membrane with a pore size of about 5 nm, thereby yielding fractionated heparin with an average molecular weight of about 20 kDa or greater, wherein at least 50% of heparin chains in the fractionated heparin have a molecular weight of 20 kDa or greater; desalting the fractionated heparin by tangential flow filtration using a desalting membrane with a pore size of about 3 nm, thereby yielding desalted heparin; and drying the desalted heparin by lyophilization to yield the BMW heparin.

BRIEF DESCRIPTION OF THE DRAWINGS

The accompanying drawings, which are incorporated in and form a part of the specification, illustrate the embodi

DETAILED DESCRIPTION

Figure 1:
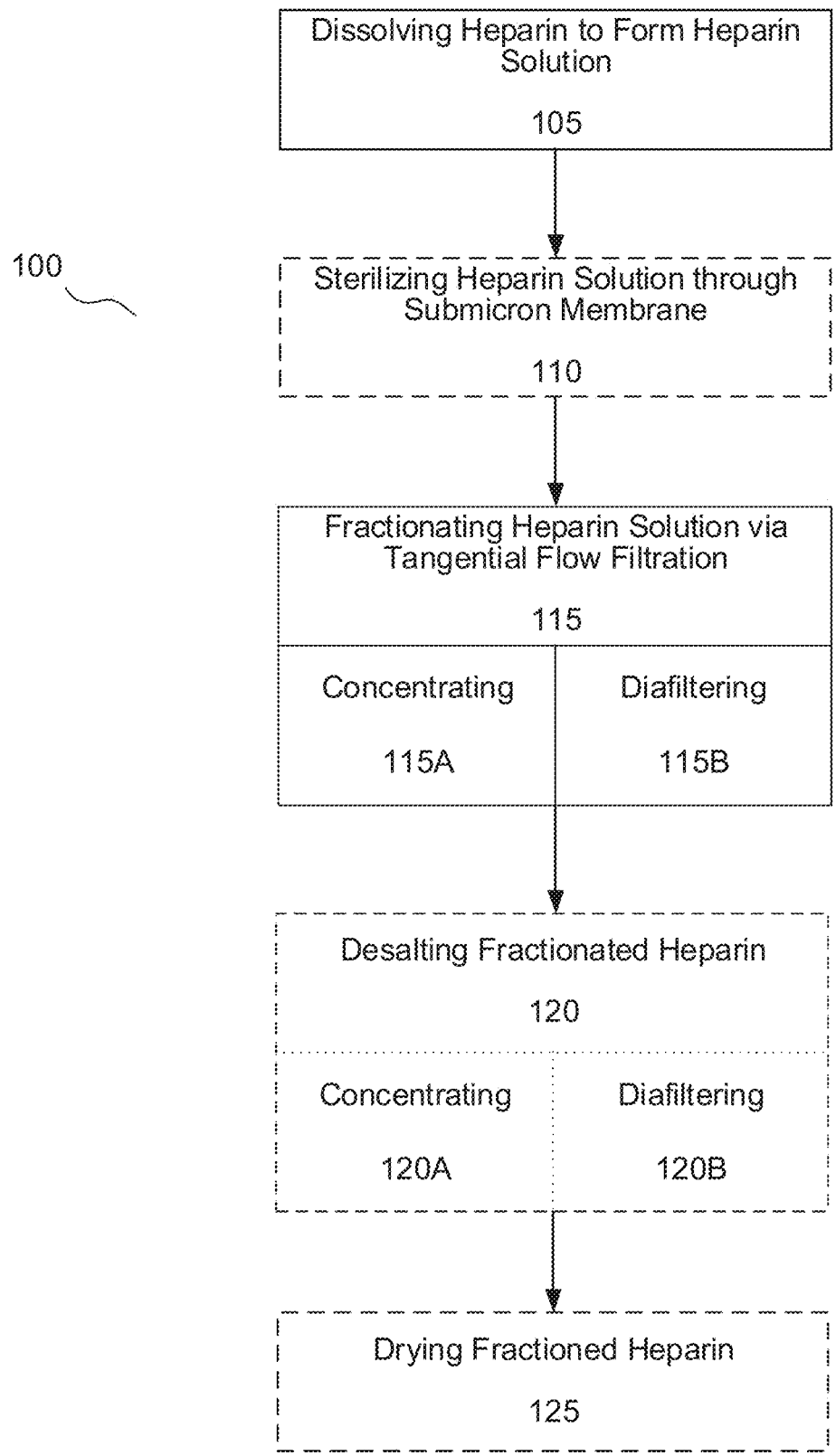
- FIG. 1 depicts a flow diagram of an illustrative method of manufacturing a high molecular weight heparin compound in accordance with an embodiment.

This disclosure is not limited to the particular systems, devices and methods described, as these may vary. The terminology used in the description is for the purpose of describing the particular versions or embodiments only, and is not intended to limit the scope. Such aspects of the disclosure may be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

All percentages, parts and ratios are based upon the total weight of the compounds and all measurements made are at about 25° C., unless otherwise specified.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, the term "therapeutic" means an agent utilized to treat, combat, ameliorate, or improve an unwanted condition or disease of a patient. In part, embodiments of the present invention are directed to the treatment of eosinophil-related inflammation and/or other eosinophil-associated diseases and conditions.

The term "effective amount" is employed herein to refer to an amount of a compound that, when administered to a subject, is appropriate for carrying out a purpose of the compound including imaging of a tissue of the subject, diagnosing a disorder in the subject, and/or monitoring of a symptom or disorder of the subject. The actual amount which comprises the "effective amount" will vary depending on a number of conditions including, but not limited to, the severity of the disorder, the size and health of the patient, the imaging modality, the manner of diagnosis, the manner of monitoring, and the route of administration. A skilled medical practitioner can readily determine the appropriate amount using methods known in the medical arts.

The term "therapeutically effective amount" is employed herein to refer to an amount of a compound that, when administered to a subject, is capable of reducing a symptom of a disorder in a subject or enhance the texture, appearance, color, sensation, or hydration of the intended tissue treatment area. The actual amount which comprises the "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government, or listed in the U.S. Pharmacopeia or other generally recognized pharmacopeia for use in mammals (e.g., animals), and more particularly, in humans.

The term "patient" and "subject" are interchangeable and may be taken to mean any living organism which may be treated with compositions of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

Where this disclosure makes reference to the term "doctor" and additional terms for various medical professionals by specific job title or role, nothing in this disclosure is intended to be limited to a specific job title or function. Doctors or medical professionals can include any doctor, nurse, medical professional, or technician. Any of these terms or job titles can be used interchangeably with the user of the systems disclosed herein unless otherwise explicitly demarcated. For example, a reference to a physician could also apply, in some embodiments to a technician, nurse, or other health care provider.

The term "tissue" refers to any aggregation of similarly specialized cells which are united in the performance of a particular function.

The term "disorder" is used in this disclosure to mean, and is used interchangeably with, the terms disease, condition, or illness, unless otherwise indicated.

The terms "administer," "administering" or "administration" as used herein refer to administering to a subject a compound (also referred to as an agent of interest), a pharmaceutically acceptable salt of the compound (agent of interest), or a composition directly by the subject or by a health care provider.

The term "treat," "treated," or "treating" as used herein refers to both therapeutic treatment, wherein the object is to reduce the frequency of, or delay the onset of, symptoms of a medical condition, or to otherwise obtain beneficial or desired clinical results. For the purposes of this invention, beneficial or desired clinical results include, but are not limited to, reversal, reduction, or alleviation of symptoms of a condition; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "diagnose," "diagnosing," or "diagnosis" as used herein refers to the process of identifying the existence and/or nature of a disease, condition, or other physiological state in a subject from its characteristics, signs and symptoms. Diagnosis may include a statement or conclusion related to the disease, condition, or other physiological state in the subject based on such a process.

The term "inhibiting" includes the administration of a composition of the present invention to prevent the onset of the symptoms, alleviating the symptoms, reducing the symptoms, delaying or decreasing the progression of the disease and/or its symptoms, or eliminating the disease, condition or disorder.

In some embodiments, the methods and compositions disclosed herein can be utilized with or on a subject in need of such examination, diagnosis, monitoring, and/or treatment, which can also be referred to as "in need thereof." As used herein, the phrase "in need thereof" means that the subject has been identified as having a need for the particular method or treatment or has been identified with a condition and that the method (e.g., imaging of a tissue, diagnosis of a condition, monitoring of a condition) or treatment has been utilized with or on the subject for that particular purpose.

The compositions produced by the methods of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration (either alone or in combination with other pharmaceuticals) can be, but are not limited to, sublingual, injectable (including short-acting, depot, implant and pellet forms injected subcutaneously or intramuscularly), topical (including nasal sprays, ointments, or creams, e.g., for application to the skin), and/or by use of vaginal creams, suppositories, pessaries, vaginal rings, rectal suppositories, intrauterine devices, and transdermal forms such as patches and creams.

Specific modes of administration will depend on the indication or purpose. The selection of the specific route of administration and the dose regimen is to be adjusted or titrated by the clinician according to methods known to the clinician in order to obtain the optimal clinical response. The amount of compound to be administered is that amount which is effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

For oral administration, the compositions can be formulated readily by the methods herein by combining high purity high molecular weight heparin with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be imaged, diagnoses, and/or treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Pharmaceutical compositions which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Capsules may also be coated with additional layers to protect the contents through one or more phases of digestion and/or delay release of the contents. For example, the capsules or other carriers may include an enteric coating (e.g., formed by a polymer) to prevent dissolution or disintegration in the gastric environment. All compositions for oral administration should be in dosages suitable for such administration.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum. Pharmaceutical compositions of the compounds may also comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

As used herein, a "mucosal tissue" is a tissue lining various cavities within the body. Examples of a mucosal tissue include, but are not limited to, mucosal tissue lining the nose, sinuses, bronchi, lungs, conjunctiva, oral cavity, tongue, esophagus, stomach, pylorus, duodenum, jejunum, ileum, ascending colon, caecum, appendix, transverse colon, descending colon, rectum, anus, urethra, and urinary bladder. A mucosal tissue comprises an epithelial surface, glandular epithelium which secretes mucus, basement membrane, and submucosa with connective tissue.

As used herein, an "eosinophil granule protein" is a protein that comprises the granules in eosinophils. When an eosinophil is activated, granule proteins are released from the cell into the surrounding tissue. The released granule proteins can cause pathologic inflammatory responses in the surrounding tissue, for example esophageal mucosal tissue. Examples of eosinophil granule proteins include, but are not limited to, major basic protein (MBP), major basic protein 1 (MBP-1), major basic protein 2 (MBP-2), eosinophil derived neurotoxin (EDN), eosinophil cationic protein (ECP), and eosinophil peroxidase (EPO). Other examples of eosinophil granule proteins are provided in Kita et al., Biology of Eosinophils, Chapter 19 of Immunology, which is hereby incorporated by reference for its teaching of examples of eosinophil granule proteins.

As used herein, "high molecular weight heparin" refers to heparin and/or heparin salts (e.g., heparin sodium) having a molecular weight of about 20 kDa or greater. Heparin polymer typically consists of a mixture of polydisperse linear polymers, i.e., having molecular chains of varying lengths, such that the molecular weight of the heparin chains varies and cannot be fully described by a single number. Accordingly, high molecular weight heparin is more particularly described as having an average molecular weight of about 20 kDa or greater. Average molecular weight may be calculated as a number average (i.e., total weight of the sample divided by the number of molecules in the sample). Furthermore, high molecular weight heparin may have a different polydispersity than unfractionated heparin as further described herein. Polydispersity may be quantified as a polydispersity index (PDI):

$$PDI = \frac{M_W}{M_N}$$

where $M_W$ is the weight average molecular weight of the sample (i.e., the sum of each molecule's molecular weight multiplied by the molecule's weight fraction of the total sample's weight) and $M_N$ is the number average molecular weight of the compound. In some instances, high molecular weight heparin may have a lower polydispersity than unfractionated heparin. In some instances, high molecular weight heparin may have a higher polydispersity than unfractionated heparin. In other instances, high molecular weight heparin may have a substantially similar polydispersity to unfractionated heparin.

As used herein, "low molecular weight heparin" refers to heparin and/or heparin salts (e.g., heparin sodium) having a molecular weight of about 8 kDa or less. For example, Enoxaparin is a product in a low molecular weight heparin family and has a molecular weight of about 4.5 kDa. Heparin polymer typically consists of a mixture of polydisperse linear polymers, i.e., having molecular chains of varying lengths, such that the molecular weight of heparin chains varies and cannot be fully described by a single number. Accordingly, low molecular weight heparin is more particularly described as having an average molecular weight of less than about 8 kDa. Average molecular weight may be calculated as a number average (i.e., total weight of the sample divided by the number of molecules in the sample). Furthermore, the polydispersity of low molecular weight heparin may vary based on the method of depolymerization. In some instances, the low molecular weight heparin may have a lower polydispersity than unfractionated heparin as further described herein. In other cases, low molecular weight heparin may have a polydispersity substantially equal to and/or greater than unfractionated heparin.

As used herein, "unfractionated heparin" or "heparin" refers to a heparin polymer with molecular chains of varying lengths, and molecular weights ranging from 3 to 30 kDa. "Unfractionated heparin" or "heparin" may have a greater polydispersity than high molecular weight heparin or low molecular weight heparin, not having been fractionated to sequester the fraction of molecules with a particular limited range of molecular weight. In other instances, unfractionated heparin may have a lower or substantially equal polydispersity to high molecular weight heparin or low molecular weight heparin.

As used herein, a "radiolabel" is an isotopic composition that can be attached to a substance, for example heparin, to track the substance as it passes through a system or tissue. A non-limiting example of a radiolabeled substance is radiolabeled heparin including, but not limited to radiolabeled high molecular weight heparin, radiolabeled low molecular weight heparin as well as radiolabeled unfractionated heparin. As provided herein, the methods described herein can be used with any of the radiolabeled heparins disclosed herein, including but not limited to radiolabeled high molecular weight heparin, radiolabeled low molecular weight heparin as well as radiolabeled unfractionated heparin. In some aspects, a radiolabeled heparin can be $^{99m}$Tc-heparin. Examples of other radiolabels include, but are not limited to, 111In, 14C, 3H, 13N, 18F, 51Cr, 125I, 133Xe, 81mKr, and 131I. Other radiolabels that can be attached to a substance, for example heparin, can be found in Table 1. A radiolabel, for example, $^{99m}$Tc, can be attached to a substance, for example heparin, using commercially available reagents well known to persons of ordinary skill in the art. In some aspects, $^{99m}$Tc-heparin can be prepared as shown in Example 5 below.

TABLE 1

Commonly utilized radiolabels.

| Nuclide | Physical half-life |
| --- | --- |
| $^{3}$H | 12.3 years |
| $^{11}$C | 20.4 minutes |
| $^{13}$N | 10 minutes |

TABLE 1-continued

Commonly utilized radiolabels.

| Nuclide | Physical half-life |
| --- | --- |
| $^{14}$C | 5730 years |
| $^{15}$O | 2 minutes |
| $^{18}$F | 110 minutes |
| $^{32}$P | 14.3 days |
| $^{51}$Cr | 27.7 days |
| $^{52}$Fe | 8.3 hours |
| $^{57}$Co | 271 days |
| $^{58}$Co | 71 days |
| $^{59}$Fe | 45 days |
| $^{60}$Co | 5.2 years |
| $^{62}$Zn | 9.3 hours |
| $^{62}$Cu | 9.7 minutes |
| $^{64}$Cu | 12.7 hours |
| $^{67}$Cu | 2.6 days |
| $^{67}$Ga | 78.2 hours |
| $^{68}$Ga | 68 minutes |
| $^{76}$Br | 16 hours |
| $^{81m}$Kr | — |
| $^{82}$Rb | 75 seconds |
| $^{82}$Sr | 25.5 days |
| $^{86}$Y | 14.74 hours |
| $^{89}$Zr | 3.27 days |
| $^{89}$Sr | 50.6 days |
| $^{90}$Sr | 28.5 years |
| $^{90}$Y | 2.7 days |
| $^{99m}$O | 66 hours |
| $^{99m}$Tc | 6.0 hours |
| $^{111}$In | 2.8 days |
| $^{113}$In | 100 minutes |
| $^{123}$I | 13.2 hours |
| $^{124}$I | 4.2 days |
| $^{125}$I | 60 days |
| $^{131}$I | 8.0 days |
| $^{133}$Xe | 5.3 days |
| $^{137}$Cs | 30 years |
| $^{153}$Sm | 1.9 days |
| $^{186}$Re | 3.8 days |
| $^{201}$Tl | 73 hours |

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason. Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As discussed herein, high molecular weight heparin may be effective for localizing to sites of eosinophil-related inflammation. Furthermore, high molecular weight heparin may be effective for neutralizing the toxic effects of MBP-1 and other eosinophil granule proteins including MBP-2, EDN, ECP, and EPO. In some embodiments, the high molecular weight heparin can function as a medication by application to or delivery to one or more sites of eosinophil-related inflammation. Furthermore, because the high molecular weight heparin can be used to target eosinophil-related inflammation, tracers and/or therapeutic agents may be conjugated to the high molecular weight heparin to provide a targeted delivery to the eosinophil-related inflammation. High molecular weight heparin compounds may be advantageous because high molecular weight heparin will bind more avidly than low molecular weight heparin to sites of eosinophil-related inflammation. In turn, the quantity of heparin (e.g., high molecular weight heparin) used for localization of eosinophil-related inflammation can be reduced with the expectation that a greater percentage of heparin will localize to the one or more sites of inflammation.

Despite these advantages, several challenges have hindered the production of high molecular weight heparin. The lack of uniformity in chain length that is inherent to heparin creates major difficulties in isolating chains of a particular molecular weight. Given the focus on low molecular weight heparin in the medical field, methods of producing low molecular weight heparin compounds have been successful. However, there has not been similar progress in developing methods of fractionating high molecular weight heparin. Further, even where heparin compounds having a targeted average molecular weight (e.g., low molecular weight heparin) have been successfully produced, the molecular weight nonetheless varies greatly such that the compounds may not have a high proportion of heparin chains within the targeted molecular weight range.

Methods of Manufacturing a High Molecular Weight Heparin Compound

Referring now to FIG. 1, a flow diagram of an illustrative method of manufacturing a high molecular weight heparin (HMWH) compound is depicted in accordance with an embodiment. As shown in FIG. 1, the method 100 comprises dissolving 105 a heparin (i.e., a starting material) to form a heparin solution and fractionating 115 the heparin solution via tangential flow filtration (TFF) using a membrane with a listed molecular weight cut off (MWCO) between about 8 kDa and about 12 kDa, e.g., about 10 kDa. According to the method 100, the TFF yields a retentate comprising fractionated heparin with an average molecular weight of 20 kDa or greater, i.e., a high molecular weight heparin compound. In some embodiments, the fractionated heparin may have a high purity, i.e., a substantial fraction of the heparin chains in the fractionated heparin have a high molecular weight as further described herein.

In some embodiments, the heparin starting material comprises unfractionated heparin (UFH). In some embodiments, the unfractionated heparin may be a heparin salt. In some embodiments, the heparin salt comprises heparin sodium, heparin calcium, and/or additional heparin salts as would be known to a person having an ordinary level of skill in the art. For example, the starting material may be USP heparin sodium, i.e., heparin sodium meeting the quality standard of the United States Pharmacopeia. Additional types of commercially available heparin formulations are also contemplated herein.

Referring once again to FIG. 1, the step of dissolving 105 the heparin starting material is now described in further detail. In some embodiments, dissolving 105 the heparin starting material comprises dissolving heparin in a salt solution. In some embodiments, the salt solution comprises a sodium chloride (NaCl) solution. However, various salt solutions may be utilized herein as would be apparent to a person having an ordinary level of skill in the art.

In some embodiments, the salt solution may be provided at a predetermined concentration, e.g., a molar concentration. The concentration of the salt solution may affect the permeability of the membrane to heparin chains. Accordingly, the concentration of the salt solution may be refined based on the desired parameters of the heparin product. For example, too low of a salt concentration may result in decreased permeability such that very few heparin chains, including those with low molecular weight, are filtered out of the retentate. Accordingly, too low of a salt concentration may result in decreased purity of the heparin product. In another example, too high of a salt concentration may result in increased permeability such that all or substantially all of the heparin passes through the membrane and are filtered out. Accordingly, too high of a salt concentration may result in decreased yield of heparin product. The molar concentration of the salt solution may therefore be adjusted and regulated to refine the effective molecular weight cut off of the membrane as it relates to heparin. In some embodiments, the salt solution may be provided at a molar concentration of about 100 mM (i.e., about 0.1 mol/L). However, various concentrations of the salt solution are contemplated herein. For example, the salt solution may comprise a molar concentration of about 50 mM, about 60 mM, about 70 mM, about 80 mM, about 90 mM, about 100 mM, about 150 mM, about 200 mM, greater than about 200 mM, or individual values or ranges therebetween.

The heparin sodium and the salt solution may be combined in various ratios during the step of dissolving 105. In some embodiments, about 2 g of heparin sodium may be combined with about 50 mL of salt solution, i.e., about 0.04 g/mL. However, it should be understood that this ratio is merely exemplary and may be modified as would be apparent to a person having an ordinary level of skill in the art. In some embodiments, the heparin sodium and the salt solution may be combined at a ratio of about 0.01 g/mL, about 0.02 g/mL, about 0.03 g/mL, about 0.04 g/mL, about 0.05 g/mL, about 0.1 g/mL, about 0.2 g/mL, greater than about 0.2 g/mL, and/or individual values or ranges therebetween. Furthermore, the process may be scaled significantly to produce larger batches of heparin product. As discussed further, the methods described herein are advantageous because they may be scaled significantly with only minor alterations to the process and without compromising the average molecular weight and/or the purity of the compound, thereby providing a commercial advantage for the production of high molecular weight heparin over conventional methods.

As shown in FIG. 1, in some embodiments, the method further comprises sterilizing 110 the heparin solution by filtering through a submicron membrane to remove microbes and/or bacteria therefrom. For example, the heparin solution may be filtered through a membrane having about 0.2 or 0.22 μm pore size. However, membranes with various pore sizes configured to sterilize fluid may be utilized.

The step of fractionating 115 the heparin solution via tangential flow filtration is now described in further detail. In order to fully convey the improvements by the methods described herein, TFF is first described generally in terms of its conventional usage. TFF (also referred to as cross-flow filtration) is a rapid filtration method for separation and purification of biomolecules. It can be applied to a wide range of biological fields, including fractionating large biomolecules from small biomolecules. Typically, TFF is designed for processing or separation of globular proteins with a consistent structure.

In a typical TFF process with globular proteins, TFF comprises concentrating target molecules in the feed solution by passing the feed solution tangentially across the surface of a membrane having pores with a predetermined molecular weight cut off (MWCO). A positive pressure may be applied on the feed side of the membrane (i.e., a back pressure) to promote circulation and passage of molecules towards the membrane. A proportion of molecules in the solution that are smaller than the MWCO permeate through the membrane, referred to as permeate or filtrate. Molecules in the solution that are larger than the MWCO are generally retained on the feed side of the membrane, referred to as retentate. Due to the removal of relatively smaller molecules and overall reduction of solution volume, the retained target molecules are concentrated in the retentate.

A typical TFF process further comprises diafiltering the retentate by adding fresh solvent to the feed to replace the removed permeate volume. In some embodiments, diafiltering is performed at intervals (i.e., discontinuous diafiltration) while concentrating takes place continuously, thereby cycling the solution through stages of concentration and dilution until the solution is adequately fractionated. In some embodiments, diafiltering may be performed continuously. For example, solvent may be added at the same rate as the permeate flow rate, i.e., the rate of concentration, such that the volume in the system remains substantially constant. In some embodiments, the total volume of solvent added to the system for filtration may be about equal to the volume of the system (i.e., 1 diafiltration volume or DV). However, additional volumes may be utilized for diafiltering, e.g., about 1 DV, about 2 DV, about 3 DV, about 4 DV, about 5 DV, about 10 DV, about 20 DV, greater than 20 DV, or individual values or ranges therebetween. Each additional DV facilitates removal of a greater number of molecules that are smaller than the MWCO, resulting in a more complete fractionation (i.e., a level of "purity" as defined and further described herein).

Turning once again to the present embodiments, it should be understood that commercially available TFF systems (e.g., the Minimate TFF system available from Pall Corporation of Port Washington, N.Y.) are conventionally used for processing globular proteins with a consistent structure. Accordingly, the expected results, including the listed MWCOs, are determined within this context. The listed MWCO of a membrane may be defined as the expected MWCO for processing globular proteins based on pore size and other factors as would be known and understood by an ordinary artisan. By contrast, heparin is a linear polysaccharide and may interact with the pores of the membrane in a different manner than a globular protein because the molecular weight of a heparin unit does not generally correspond to a diameter of the molecule. As a result, the listed MWCO of commercially available membranes may be inaccurate when used with heparin. For example, heparin chains having molecular weights above the listed MWCO may pass through the membrane at substantial rates such that an effective MWCO is greater than the listed MWCO (see, e.g., Examples 1-3 herein). This finding is beyond the scope of the conventional TFF processes and demonstrates that membrane pore size is but one of many factors that affects the MWCO for TFF of linear polysaccharides. Due to heparin's inherent heterogeneity and variable polymer chain length, many of the conditions under which TFF 15 performed may alter the effective MWCO. For example, the effective MWCO may be variable based on a combination of factors including membrane pore size, salt concentration, and applied pressure. Accordingly, these factors may be refined to control the effective MWCO, i.e., adjust the effective MWCO up or down with respect to the listed MWCO. It should also be understood that molecules smaller than the MWCO may be retained in some quantity and molecules larger than the effective MWCO may be removed in some quantity, i.e., the effective MWCO under a particular set of conditions is not absolute. Rather, a particular set of conditions generally facilitates removal of molecules smaller than the effective MWCO and retention of molecules larger than the effective MWCO. For example, MWCO and/or Nominal Molecular Weight Cutoff (NMWCO) may generally be defined for a membrane or other filtration component as the lowest molecular weight for a solute at which greater than 90% of the solute is retained by the membrane. Accordingly, the MWCO may objectively measure the permeability of a membrane in a manner defined and understood generally by a person having an ordinary level of skill in the art. Furthermore, as discussed herein, the MWCO may be based on processing of globular proteins and thus an effective MWCO may differ with respect to non-globular proteins.

Referring once again to FIG. 1, the step of fractionating 115 the heparin solution via tangential flow filtration may comprise concentrating 115A the heparin solution and diafiltering 115B the heparin solution using a membrane with a predetermined MWCO. In some embodiments, TFF is performed using a membrane with a listed MWCO of about 10 kDa. In some embodiments, TFF is performed using a membrane with a listed MWCO in the range of about 8 kDa to about 12 kDa. However, other listed MWCOs may be utilized for TFF under an appropriate set of conditions as described herein (i.e., with modifications to the salt concentration, applied pressure, total run time, total filtration volume, and the like) to produce a desired effective MWCO. For example, TFF may be performed with a membrane with a listed MWCO of about 3 kDa, about 4 kDa, about 5 kDa, about 6 kDa, about 7 kDa, about 8 kDa, about 9 kDa, about 10 kDa, about 12 kDa, about 14 kDa, about 16 kDa, 18 about kDa, about 20 kDa, greater than about 20 kDa, or individual values or ranges therebetween.

In some embodiments, MWCO may relate to a size and/or diameter of pores and/or openings through the membrane material. Accordingly, in some embodiments, the membrane used for performing TFF may be described with respect to a nominal or average pore size of the membrane. In some embodiments, TFF is performed using a membrane having an average pore size (i.e., diameter) of about 5 nm. In some embodiments, TFF may be performed using a membrane having an average pore size (i.e., diameter) of about 4 nm to about 6 nm. However, other pore sizes may be utilized for TFF under an appropriate set of conditions as described herein (i.e., with modifications to the salt concentration, applied pressure, total run time, total filtration volume, and the like) to produce a desired effective MWCO. For example, TFF may be performed with a membrane having an average pore size of about 3 nm, about 3.5 nm, about 4 nm, about 4.5 nm, about 5 nm, about 5.5 nm, about 6 nm, about 6.5, about 7 nm, about 7.5, about 8 nm, about 8.5 nm, about 9 nm, about 9.5 nm, about 10 nm, greater than about 10 nm, or individual values or ranges therebetween. It should also be understood that pore sizes may not be consistent within a membrane material and may vary greatly across a membrane material. Accordingly, pore sizes beyond the ranges explicitly described herein may be implemented in some cases under an appropriate set of conditions to produce a desired effective MWCO.

In some embodiments, the membrane may be a polyethersulfone (PES) membrane. In one specific example, the membrane may be a PES membrane with polyolefin support in the form of a cassette or other standard membrane structure (e.g., the T-Series TFF Cassettes available from Pall Corporation of Port Washington, N.Y.). In additional embodiments, the membrane may be a hollow fiber membrane (e.g., the Microza Hollow Fiber Membrane Systems available from Pall Corporation of Port Washington, N.Y.). For example, the hollow fiber membrane may be formed using polyvinylidene fluoride (PVDF) and/or polyacrylonitrile (PAN). In some embodiments, a hollow fiber membrane may result in higher speed, efficiency, and/or overall yield of the filtration process as compared to other conventional membrane materials. For example, hollow fiber membranes may reduce clogging and thus improve the speed and efficiency of the filtration. However, it should be understood that various membranes materials may be utilized as would be known to a person having an ordinary level of skill in the art and may be selected to improve the scale, yield, speed, efficiency, capacity, cost, and/or other parameters of the filtration procedure.

In some embodiments, the membrane may utilize a porous and/or non-woven support. For example, the support may be formed from polyolefin. In another example, the support may be formed from acrylonitrile butadiene styrene (ABS). In another example, the support may be formed from polyvinyl chloride (PVC). However, it should be understood that various support materials may be utilized as would be known to a person having an ordinary level of skill in the art.

In some embodiments, the applied pressure during TFF may be about 29 psi (see Examples 1-2). In some embodiments, the applied pressure during TFF may be about 30 psi (see Example 3). However, the applied pressure may be varied with appropriate corresponding conditions to produce a desired effective MWCO. For example, the applied pressure may be about 1 psi, about 5 psi, about 10 psi, about 15 psi, about 20 psi, about 25 psi, about 30 psi, or individual values or ranges therebetween.

In some embodiments, the total filtration volume used for diafiltration 115B may be about 1800 mL, i.e., 36 DVs. In some embodiments, the total filtration volume used for diafiltration may be about 2050 mL, i.e. 41 DVs. It should be understood that, because the total filtration volume affects the amount of lower molecular weight particles removed through TFF, the selected total filtration volume may also affect the "purity" of the fractionated heparin as defined and described herein. In some embodiments, a purity of the fractionated heparin may be directly related to total filtration volume. Accordingly, the total filtration volume may be varied with appropriate corresponding conditions to produce a desired effective MWCO. For example, the total filtration volume may be about 5 DVs, about 10 DVs, about 20 DVs, about 30 DVs, about 40 DVs, about 50 DVs, about 100 DVs, or individual values or ranges therebetween.

In some embodiments, the fractionating 115 the heparin solution via TFF yields a retentate comprising fractionated heparin with an average molecular weight greater than the average molecular weight of the heparin starting material. In some embodiments, the average molecular weight of the fractionated heparin is at least about 20 kDa, i.e., a HMWH compound (see Examples 1-3 where the average molecular weight is above 20 kDa). However, in some embodiments, the fractionated heparin comprises an average molecular weight of greater than about 20 kDa. For example, the fractionated heparin may comprise an average molecular weight of about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 35 kDa, about 40 kDa, greater than about 40 kDa, or individual values or ranges therebetween.

In some embodiments, the fractionated heparin has a high purity. The purity of the fractionated heparin may be defined as the amount of heparin chains having a molecular weight above a predetermined threshold. For example, the predetermined threshold may be about 20 kDa and accordingly the purity of the fractionated heparin may be determined based on a fraction, percentage, or ratio of heparin chains with a molecular weight of 20 kDa or greater compared to those having a molecular weight of less than about 20 kDa (i.e., the proportion that are high molecular weight heparin). In some embodiments, the fractionated heparin may have a purity of heparin chains at or above 20 kDa of at least about 50%, i.e., "high purity" (see Examples 1-3 where the average molecular weight is above 20 kDa). In additional embodiments, the fractionated heparin may have a purity of heparin chains at or above 20 kDa of about 60%, about 70%, about 80%, about 90%, about 95%, greater than about 95%, or individual values or ranges therebetween.

In some embodiments, the fractionated heparin may be additionally characterized by a maximum quantity of molecular chains with a molecular weight below the predetermined threshold. For example, the fractionated heparin may comprise a percentage of heparin chains with a molecular weight below 20 kDa at or below about 50%, about 40%, about 30%, about 25%, about 20%, about 15%, about 10%, about 5%, less than about 5%, or individual values or ranges therebetween. In additional embodiments, the fractionated heparin may be additionally characterized by a maximum amount of low molecular weight heparin chains therein, i.e., the amount of heparin chains having a molecular weight below a cutoff defining low molecular weight heparin (e.g., about 8 kDa). For example, the fractionated heparin may comprise a percentage of heparin chains with a molecular weight below about 8 kDa at or below about 50%, about 40%, about 30%, about 25%, about 20%, about 15%, about 10%, about 5%, less than about 5%, or individual values or ranges therebetween.

Additionally, in some embodiments the predetermined threshold may be a value other than about 20 kDa. For example, the predetermined threshold may be set based on the minimum desired average molecular weight for the fractionated heparin. In some embodiments, the predetermined threshold for assessing purity of the fractionated heparin may be about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 35 kDa, about 40 kDa, greater than about 40 kDa, or individual values or ranges therebetween. Similarly, the cutoff of the low molecular weight chains may be a value other than about 8 kDa. For example, the cutoff may be about 5 kDa, about 6 kDa, about 7 kDa, about 8 kDa, about 9 kDa, about 10 kDa, about 11 kDa, about 12 kDa, greater than about 12 kDa, or individual values or ranges therebetween.

As described herein, characteristics of the resulting fractionated heparin may be controlled by the conditions of the TFF process in the fractionating 115 step. For example, the average molecular weight and/or the purity of the fractionated heparin may vary based on a combination of factors including membrane pore size (i.e., listed MWCO), salt concentration, applied pressure, total run time, and total filtration volume. Accordingly, these factors may be regulated to generate fractionated heparin with the desired characteristics.

In one particular example, the average molecular weight of the fractionated heparin may be selected as 20 kDa or greater and the purity of the fractionated heparin may be selected as 50% or greater. Accordingly, dissolving 105 may be performed using an about 100 mM NaCl solution. Further, concentrating 115A the heparin solution may be performed using a membrane with a listed MWCO of about 10 kDa and an applied pressure of about 29-30 psi. Additionally, diafiltering 115B the heparin solution may be performed using an about 100 mM NaCl solution and a total filtration volume of about 36-41 DVs, e.g., about 1800-2050 mL. As shown in Examples 1-3, these conditions may yield a fractionated heparin having an average molecular weight of 20 kDa or greater and a purity of 50% or greater.

When fractionating 115 is complete, the retentate may be recovered from the feed side of the membrane. Further, the membrane may be washed with deionized water to yield a wash volume. Because the wash volume may contain high molecular weight heparin that collected on the membrane during fractionating 115, the wash volume may be combined with the retentate in order to improve the yield of fractionated heparin.

Referring once again to FIG. 1, the method 100 may further comprise desalting 120 the fractionated heparin. In some embodiments, desalting 120 may be performed via TFF with appropriate selected conditions.

In some embodiments, desalting 120 may comprise concentrating 120A the fractionated heparin using a membrane with a MWCO configured to generally prohibit passage of the fractioned heparin and permit passage of the salts and/or ions thereof in the salt solution. In some embodiments, a membrane with a MWCO of about 3 kDa may be used. However, membranes with a MWCO of about 1 kDa, about 3 kDa, about 5 kDa, greater than about 5 kDa, or individual values or ranges therebetween may be utilized herein. In some embodiments, the fractionated heparin may be concentrated 120A under an applied pressure of about 29-30 psi. However, the applied pressure may be varied as would be apparent to a person having an ordinary level of skill in the art.

In some embodiments, desalting 120 may further comprise diafiltering 120B the fractionated heparin using deionized water. In some embodiments, diafiltering 120B may be performed with a total filtration volume of about 10 DVs, e.g., about 500 mL. However, the total filtration volume may be varied as would be apparent to a person having an ordinary level of skill in the art.

While exemplary processes for desalting 120 the fractionated heparin are described herein, it should be understood that various conventional methods of desalting may be utilized herein as would be apparent to a person having an ordinary level of skill in the art.

Referring once again to FIG. 1, the method 100 may further comprise drying 125 the fractionated heparin, thereby producing an isolated HMWH compound. In some embodiments, drying 125 may be performed by lyophilization. However, it should be understood that drying 125 may be performed by any conventional means as would be apparent to a person having an ordinary level of skill in the art.

As shown in Examples 1-3, the disclosed methods may produce the HMWH compound at a yield of about 15-18%. In some embodiments, the methods may be modified in various manners to improve the yield of the HMWH compound. In some embodiments, the membrane pore size, salt concentration, applied pressure, and/or total filtration volume used for fractionation may be adjusted in a manner that improves the yield. For example, reducing applied pressure may result in slower fractionation (i.e., higher total run time for a given filtration volume) with an improved yield. In another example, reducing the total filtration volume may result in faster fractionation (i.e., lower total run time for a given filtration volume) with an improved yield. In another example, reducing the membrane pore size may result in fractionation with an improved yield. Adjusting the salt concentration may similarly result in improvements to the yield of the methods disclosed herein.

In some embodiments, using a heparin starting material with a higher average molecular weight may similarly result in a higher yield. For example, use of a heparin starting material that is pre-filtered by molecular weight may result in a higher yield. In another example use of a heparin starting material that is pre-filtered by a characteristic that roughly correlates to molecular weight may also result in a higher yield.

In some embodiments, the methods disclosed herein may produce additional useful byproducts. For example, the filtrate or permeate (i.e., the material removed from the retentate via TFF) may comprise heparin with a substantially reduced average molecular weight. In some embodiments, the permeate may comprise a LMWH. In some embodiments, the permeate may be processed to produce a LMWH through additional fractionation steps. Such fractionation steps would be known to a person having an ordinary level of skill in the art. Accordingly, the methods disclosed herein could be used, with or without additional steps, to produce a LMWH compound as a byproduct alongside the HMWH compound.

While the exemplary methods described herein utilize tangential flow filtration for producing fractionated heparin from an unfractionated heparin starting material, it should be understood that additional types of filtration may be utilized to accomplish this step. In additional embodiments, alternative types of mechanical filtration as would be known to a person having an ordinary level of skill in the art may be utilized for fractionating the heparin. Accordingly, some or all of the remaining steps as described herein may be used in conjunction with such alternative manners of filtration in order to produce the final high molecular weight heparin compound.

It should be understood that the presently disclosed methods are advantageous because attempts to produce isolated HMWH compounds by conventional methods of filtering by molecular weight would encounter various difficulties. Generally, the linear structure of heparin and the inherent heterogeneity in terms of polymer chain length (and thus molecular weight) hinders the ability to fractionate heparin for higher molecular weights with substantial purity by conventional methods. However, the methods disclosed herein demonstrate the unexpected finding that fractionation of heparin by TFF using membranes intended for globular proteins may produce heparin fractions with an average molecular weight of 20 kDa or greater, where 50% or more of the heparin chains having a molecular weight of 20 kDa or greater. Further, these characteristics of the resulting heparin fractions may be carefully tailored by regulating the conditions of TFF including membrane pore size, salt concentration, applied pressure, and filtration volume.

The disclosed methods are additionally advantageous due to their scalability. For example, while it may be possible to produce HMWH compounds by gel permeation chromatography, such a process would be difficult to scale because of its relatively high cost and additional difficulties when large volumes are utilized. Other types of membrane filtration may. entail a high degree of fouling (i.e., buildup on the membrane) that causes clogging and additional difficulties when high filtration volumes and/or run times are involved. By contrast, TFF is relatively low cost and by its very nature entails a low degree of fouling. Accordingly, TFF is extremely scalable and can be used to fractionate thousands of liters of solution with little added cost. Accordingly, the methods disclosed herein are very scalable for manufacturing purposes as compared to other processes.

The methods as described herein are not intended to be limited in terms of the particular embodiments described, which are intended only as illustrations of various features. Many modifications, variations, and additions to the methods can be made without departing from their spirit and scope, as will be apparent to those skilled in the art.

The HMWH compound may be useful for forming a HMWH composition for various medical applications. In some embodiments, the method further comprises combining the HMWH compound with a pharmaceutically acceptable excipient to produce a HMWH composition. In some embodiments, the HMWH composition may be useful for imaging, diagnosis, and/or treatment of a medical condition.

In some embodiments, the HMWH composition may be configured for binding and/or localization to eosinophil-related inflammation or expression of an eosinophil-related condition. In some embodiments, the average molecular weight of the HMWH compound and/or the purity of the HMWH compound may be selected to optimize binding to sites expressing eosinophil-related inflammation. Because HMWH exhibits a higher affinity for MBP-1 than low molecular weight heparin (LMWH) or unfractionated heparin (UFH), HMWH will bind more avidly than LMWH or unfractionated heparin UFH to sites of eosinophil-related inflammation.

In some embodiments, the binding affinity of the HMWH composition is directly related to molecular weight and thus increases with the average molecular weight of the HMWH compound. Accordingly, as the average molecular weight of the HMWH increases, the quantity of heparin required for localization of eosinophil-related inflammation may be reduced with the expectation that a greater percentage of administered heparin will localize to the inflammation sites.

In some embodiments, the localization rate of the HMWH composition is directly related to molecular weight and thus increases as the purity of the HMWH compound increases. Accordingly, as the purity of the HMWH increases, the quantity of heparin required for adequate localization of eosinophil-related inflammation may be reduced with the expectation that a greater percentage of administered heparin will localize to the inflammation sites. Likewise, where a higher molecular weight threshold is used to define purity as described herein, the localization rate may similarly increase.

The HMWH compositions produced by the methods herein may be configured for administration in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration (either alone or in combination with other pharmaceuticals) can be, but are not limited to, sublingual, injectable (including short-acting, depot, implant and pellet forms injected subcutaneously or intramuscularly), topical (including ointments or creams, e.g., for application to the skin), and/or by use of vaginal creams, suppositories, pessaries, vaginal rings, rectal suppositories, intrauterine devices, and transdermal forms such as patches and creams. Specific modes of administration will depend on the indication or purpose. It should also be noted that the risk of HIT and/or HITT suspected to be associated with high molecular weight heparin is limited to systemic administration. Accordingly, topical and/or oral administration advantageously do not pose a significant risk of HIT and/or HITT.

In some embodiments, the HMWH composition may be configured for imaging eosinophil-related conditions and/or other targeted condition to which HMWH localizes. Accordingly, the method may further comprise conjugating a tracer such as a radiolabeled contrast agent to the HMWH compound. For example, the radiolabeled contrast agent may be $^{99m}Tc$. Additional tracers, such as tracers used for positron emission tomography, can also be employed for detecting the binding of the HMWH to sites of eosinophil-related inflammation. In some embodiments, the tracers may be any tracer or label in Table 1. Accordingly, the HMWH composition may be administered and used to visualize the targeted condition with conventional imaging modalities, including but not limited to single photon emission computed tomography (SPECT), positron emission (PET) scans, conventional or computed tomography (CT), magnetic resonance imaging (MRI), or combinations thereof. The HMWH composition with a tracer may also be utilized for diagnosis and/or monitoring of a targeted condition based on images captured as described. In some embodiments, the HMWH composition may enable reduction of the quantity of the tracer that must be administered to the patient for adequate imaging of a site of a targeted condition (e.g., eosinophil-related inflammation). For example, due to the avidity and localization rate of the HMWH to the site, the quantity (or dose) of administered tracer may be reduced because a greater proportion of the HMWH composition localizes to the site as compared to unfractionated heparin or low molecular weight heparin. Accordingly, where the tracer is radioactive, the quantity of radioactivity that is required for adequate imaging is thereby reduced, thus improving the safety of the composition and limiting any effects associated with the administration of the radiolabeled contrast agent.

In some embodiments, the HMWH composition may be configured for treatment of eosinophil-related conditions and/or other targeted conditions expressing toxins to which HMWH localizes. Accordingly, the method may further comprise conjugating a therapeutic agent to the HMWH composition. In some embodiments, the HMWH composition further comprises a therapeutically effective amount of the therapeutic agent for administration to a patient. In some embodiments, the therapeutic agent is configured to have a therapeutic effect on the targeted condition. Due to the avidity and localization rate of the HMWH compound for a site of the targeted condition (e.g., eosinophil-related inflammation), the quantity (or dose) of the therapeutic agent needed for proper care may be reduced, thus limiting any side effects associated with the administration of the therapeutic agent. Accordingly, the therapeutically effective amount of the therapeutic agent may be less than a therapeutically effective amount typically associated with administration of the therapeutic agent in the absence of the HMWH compound or another targeted mechanism. In some embodiments, the therapeutic agent is a glucocorticoid. In some embodiments, the glucocorticoid is one or more of mometasone, fluticasone, budesonide, and solumedrol. Additional therapeutic agents are contemplated herein as would be apparent to a person having an ordinary level of skill in the art.

In some embodiments, the HMWH may include various additional components or additives as would be known to a person having an ordinary level of skill in the art. In some embodiments, the method further comprises adding a stabilizing agent to the HMWH composition. In some embodiments, the method further comprises adding a taste-masking agent to the HMWH composition.

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples:

EXAMPLES

Example 1—Tangential Flow Filtration for Production of HMWH Composition|Batch 1

Methods. 2.0132 g of USP heparin was dissolved in 50 mL of 100 mM NaCl solution and filtered through a 0.22-micron membrane. The heparin solution was then filtered with a Tangential Flow Filtration (TFF) system. A 10 kDa molecular weight cut off (MWCO) membrane was installed in the TFF system and washed with deionized water before processing. The heparin solution was then loaded into the TFF system and filtration was performed with a back pressure of 29 psi. 100 mM NaCl replacement solution was added during filtration to maintain a constant retentate volume (i.e., diafiltration). When the total volume of permeate reached 1800 mL, the process was stopped. The retentate was then desalted and dried as described in Example 4 to yield the HMWH composition.

Results. The process produced 297 mg of heparin at a yield of 15%. The composition had an average molecular weight of 23.9 kDa (i.e., overall high molecular weight). Furthermore, 56% of the heparin chains in the HMWH composition had a molecular weight greater than 20 kDa (i.e., high purity). Anti-factor Xa and anti-factor IIa assays were also performed on the composition to determine a ratio of anti-Xa:anti-IIa activity, which is relevant to therapeutic benefit of heparin as an anticoagulant. The results of Example 1 are summarized in Table 2.

TABLE 2

Analytical summary of Batches 1-3 of production of high molecular weight heparin composition by tangential flow filtration method. See Examples 1-3 for additional discussion.

| Batch No. | Ave. Molecular Wt. | Purity (% with MW > 20,000) | Anti-IIa Activity | Anti-Xa Activity | Xa:IIa Activity Ratio | Total mass | Yield (%) |
|---|---|---|---|---|---|---|---|
| 1 | 23.9 kDa | 56 | 252 U/mg | 210 U/mg | 0.8 | 297 mg | 15 |
| 2 | 23.5 kDa | 54 | 229 U/mg | 204 U/mg | 0.9 | 327 mg | 16 |
| 3 | 23.3 kDa | 53 | 221 U/mg | 196 U/mg | 0.9 | 358 mg | 18 |

Example 2—Tangential Flow Filtration for Production of HMWH Composition|Batch 2

Methods. 2.0801 g of USP heparin was dissolved in 52 mL of 100 mM NaCl solution and filtered through a 0.22-micron membrane. The heparin solution was then filtered with a TFF system. A 10 kDa MWCO membrane was installed in the TFF system and washed with deionized water before processing. The heparin solution was then loaded into the TFF system and filtration was performed with a back pressure of 29 psi. 100 mM NaCl replacement solution was added throughout filtration to maintain a constant retentate volume (i.e., diafiltration). When the total volume of permeate reached 2050 mL, the process was stopped. The retentate was then desalted and dried as described in Example 4 to yield the HMWH composition.

Results. The process produced 327 mg of heparin for at a yield of 16%. The composition had an average molecular weight of 23.5 kDa (i.e., overall high molecular weight). Furthermore, 54% of the heparin chains in the HMWH composition had a molecular weight greater than 20 kDa (i.e., high purity). Anti-factor Xa and anti-factor IIa assays were also performed on the composition to determine a ratio of anti-Xa:anti-IIa activity, which is relevant to therapeutic benefit. The results of Example 2 are summarized in Table 2.

Example 3—Tangential Flow Filtration for Production of HMWH Composition|Batch 3

Methods. 2.1476 g of USP heparin was dissolved in 54 mL of 100 mM NaCl solution and filtered through a 0.22-micron membrane. The heparin solution was then filtered with a TFF system. A 10 kDa MWCO membrane was installed in the TFF system and washed with deionized water before processing. The heparin solution was then loaded into the TFF system and filtration was performed with a back pressure of 30 psi. 100 mM NaCl replacement solution was added throughout filtration to maintain a constant retentate volume (i.e., diafiltration). When the total volume of permeate reached 2050 mL, the process was stopped. The retentate was then desalted and dried as described in Example 4 to yield the HMWH composition.

Results. The process produced 358 mg of heparin for a total yield of 18%. The composition had an average molecular weight of 23.3 kDa (i.e., overall high molecular weight). Furthermore, 53% of the heparin chains in the HMWH composition had a molecular weight greater than 20 kDa (i.e., high purity). Anti-factor Xa and anti-factor IIa assays were also performed on the composition to determine a ratio of anti-Xa:anti-IIa activity, which is relevant to therapeutic benefit. The results of Example 3 are summarized in Table 2.

Example 4—Desalting and Drying of Retentate

Methods. Following TFF with a 10 kDa MWCO membrane, the retentate was recovered from the system. The membrane was separately washed with deionized water prior to removal from the TFF system, thereby yielding a wash volume. The wash volume was combined with the retentate for desalting. A 3 kDa MWCO membrane was installed in the TFF system and washed with DI water. The retentate/wash volume mixture was then loaded and diafiltered against deionized water to remove salts therefrom. When a total volume of permeate reached 10 times the retentate volume, the desalting process was stopped.

Example 5—Preparation of $^{99m}$Tc-Heparin

Solutions of stannous chloride (40 mg/mL, Sigma 243523) were prepared in deionized water under flowing nitrogen. A 0.5 mL aliquot was filtered and mixed with 1.00 mL NaCl (1.00 M) plus 150 mg of preservative-free heparin (10,000 IU/mL). Approximately 100 mCi of freshly eluted $^{99m}$Tc was added and mixed for 30 minutes at room temperature. Aliquots containing approximately 10 mCi of $^{99m}$Tc and 20 mg of heparin were removed for tissue experiments.

Results. Labeling affinity was measured by paper chromatography Whatman number 31 with acetone, which confirmed greater than 97% binding of heparin to $^{99m}$Tc.

The heparin was also analyzed by Sephadex G25 column chromatography (HiTrap 5 mL desalting columns, GE healthcare, 17140801) with 0.15 M NaCl as the elution buffer, and approximately 1 mL fractions were collected. The test demonstrated that all of the $^{99m}$Tc eluted at the void volume and confirmed that there was no unbound $^{99m}$Tc in the radiolabeled heparin.

The stability of $^{99m}$Tc-heparin in an acidic environment was tested by diluting in artificial gastric juice (Carolina, 864603) and showing that its properties were unaltered, using both paper chromatography and Sephadex G25.

Example 6—Heparin Binding to eMBP-1 by SPR

The purpose of this study is to determine the apparent dissociation rate constants ($k_d$) for seven heparin samples binding to recombinant human (rhu) eMBP using surface plasmon resonance (SPR) Biacore technology. The goal will be to determine if there is a correlation between the complex half-life and the molecular mass of heparin.

Methods. Unfractionated and fractionated heparin samples (i.e., analytes) were assessed for binding to surfaces of recombinant human (rhu) eMBP1 (i.e., ligand).

Assay conditions: Biosensor analysis was conducted at 25° C. in an HBS buffer system (10 mM HEPES pH 7.4 and 150 mM NaCl) using a Biacore 3000 optical biosensor equipped with a CM4 sensor chip (GE, Marlborough, Mass.; BR100539). The auto-sampler was at room temperature.

Surface Preparation: Using thiol coupling chemistry, eMBP1 was immobilized to a chip surface. The thiol coupling kit protocol (Cytiva Life Sciences; Marlborough, Mass.) was followed by first activating the surface with 0.2 M EDC and 0.05 M NHS for 2 minute followed by a 4 minute injection of 80 mM PDEA in 50 mM sodium borate buffer (pH 8.5), at a flow rate of 10 µL/min. eMBP1 was diluted to 0.6 µM or 0.06 µM in 10 mM sodium acetate (pH 5.25) and injected until the targeted immobilization level was achieved. Finally, the remaining free cysteines were blocked with the injection of 50 mM L-cysteine in 0.1 M sodium acetate, 1.0 M sodium chloride (pH 4.0) for 4 minutes at 10 µL/min. The reference flow cell was produced using the same immobilization procedure but without the addition of eMBP1. rhu eMBP1 was captured to flow cells 2 through 4 (i.e., FC2, FC3, and FC4) of the sensor chip to several different densities in relative units: a low (1000 RU), medium (3000 RU), and high (4000 RU) density, respectively. A second chip was prepared in the same manner to several different densities: a low (500 RU), medium (800 RU), and high (1200 RU) density, respectively.

Analyte Preparation: Analyte concentration series ranging from 10 µg/mL to 10 ng/mL were prepared using 10-fold dilutions in running buffer.

Interaction Parameters: Injections of analyte were made in duplicate or triplicate in the order of the sample number. Multiple blank (buffer) injections were run and used to assess and subtract system artifacts. The association phases for all analyte concentrations were monitored for 600 seconds at a flow rate of 25 µL/min while the dissociation phases were collected for 1800 seconds at a flow rate of 25 µL/min.

Surface Regeneration: At the end of each binding cycle the surface was regenerated with 2, 3 (s) pulses of 6 M Guanidine, at a flow rate of 100 µL/min.

Data Analysis: The data were aligned, double referenced, and fit using Scrubber v2.0 software (BioLogic Software Pty Ltd, Campbell, Australia), which is an SPR data processing and non-linear least squares regression fitting program. The dissociation phase data were globally fit to a simple exponential decay model for each sample and assay condition. This simple decay model was an under simplification of the complex dissociation occurring between the multiple dissociation events resulting from the polydisperse analytes complexed with eMBP1 surfaces.

Results. Overall, an apparent linear response was observed between complex half-life and heparin molecular weight under certain conditions dependent upon the eMBP1 surface density and heparin concentrations. Summary data of the correlation between complex half-life and heparin molecular weight is provided in Table 3.

TABLE 3

Summary correlation plots of flow cells of Chips 1 and 2 showing correlation between complex half-life and molecular weight of the heparin sample. For Chip 1, heparin samples were injected in duplicate. For Chip 2, heparin samples were injected in triplicate. See Example 6 for additional discussion.

| Chip No. | eMBP1 Density (RU) | 10 ng/mL Heparin ($R^2$) | 100 ng/mL Heparin ($R^2$) | 10 µg/mL Heparin ($R^2$) |
|---|---|---|---|---|
| 1 | 4000 | 0.919 | NA | 0.3055 |
|   | 3000 | 0.2518 | NA | 0.5478 |
|   | 1000 | 0.4791 | NA | 0.9061 |
| 2 | 1200 | 0.5001 | 0.9772 | 0.8935 |
|   | 800 | 0.6036 | 0.9669 | 0.7448 |
|   | 500 | 0.6795 | 0.8687 | 0.7054 |

Figure 2A:
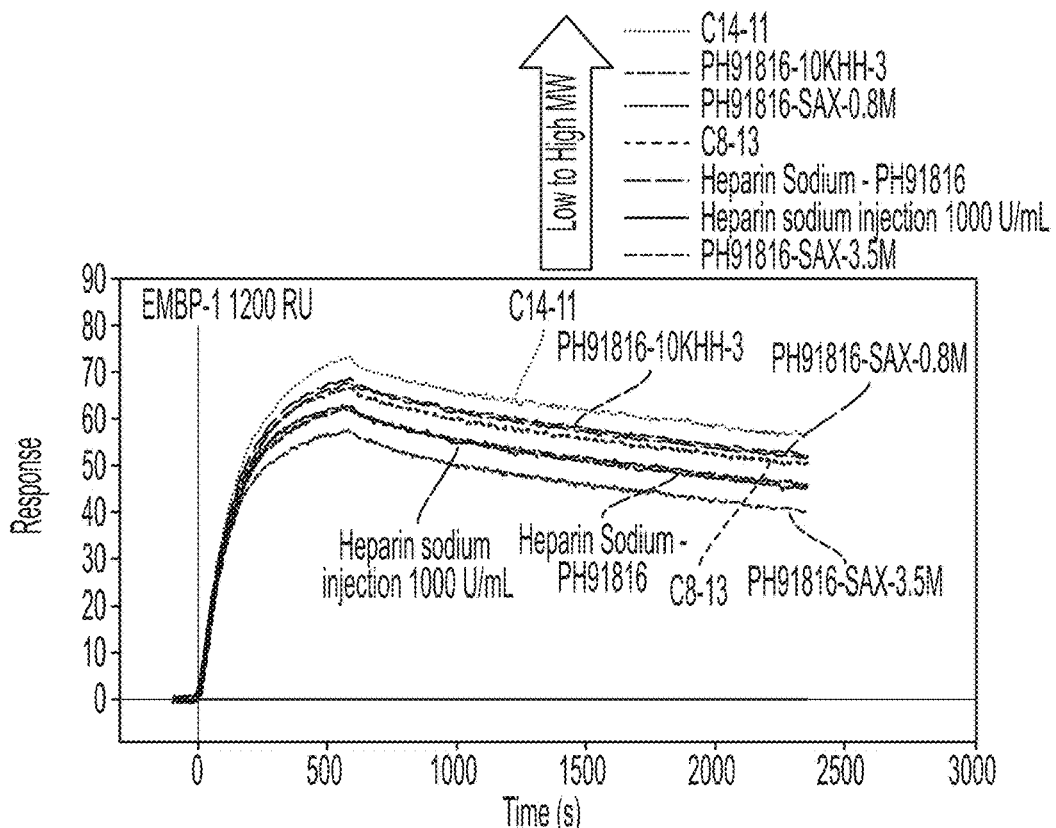
FIGS. 2A-2B depict sensorgrams of the signal response for fractionated heparin samples (i.e., analytes) binding to rhu eMBP1 (i.e., ligand) in accordance with an embodiment.
Figure 2B:
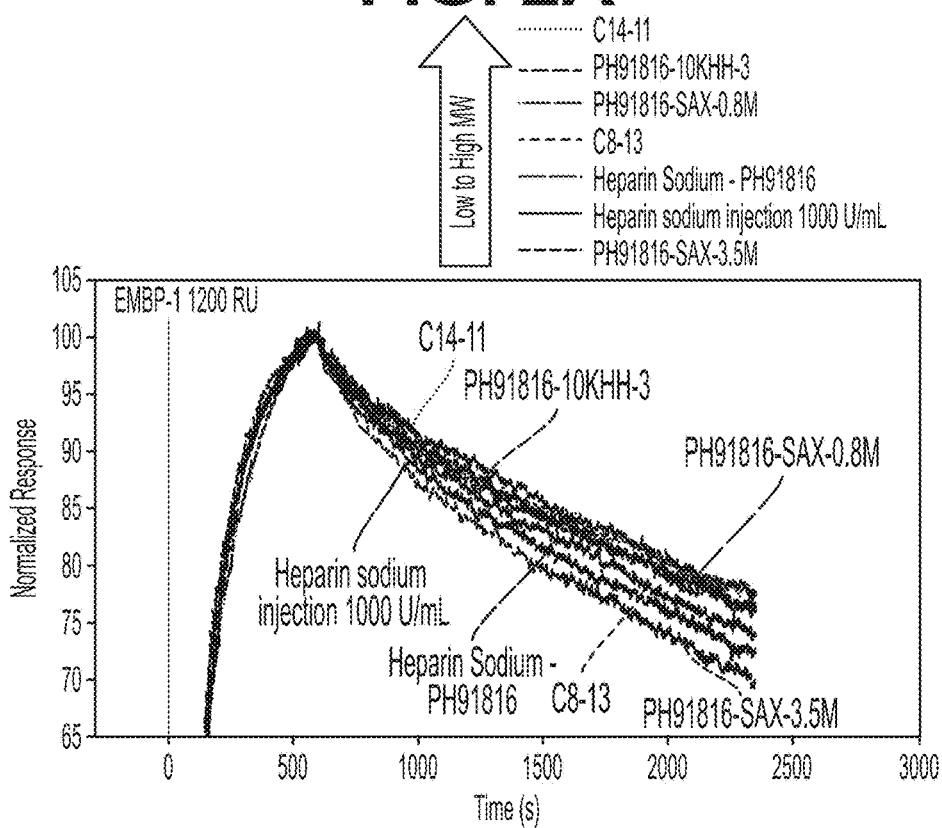
Figure 3:
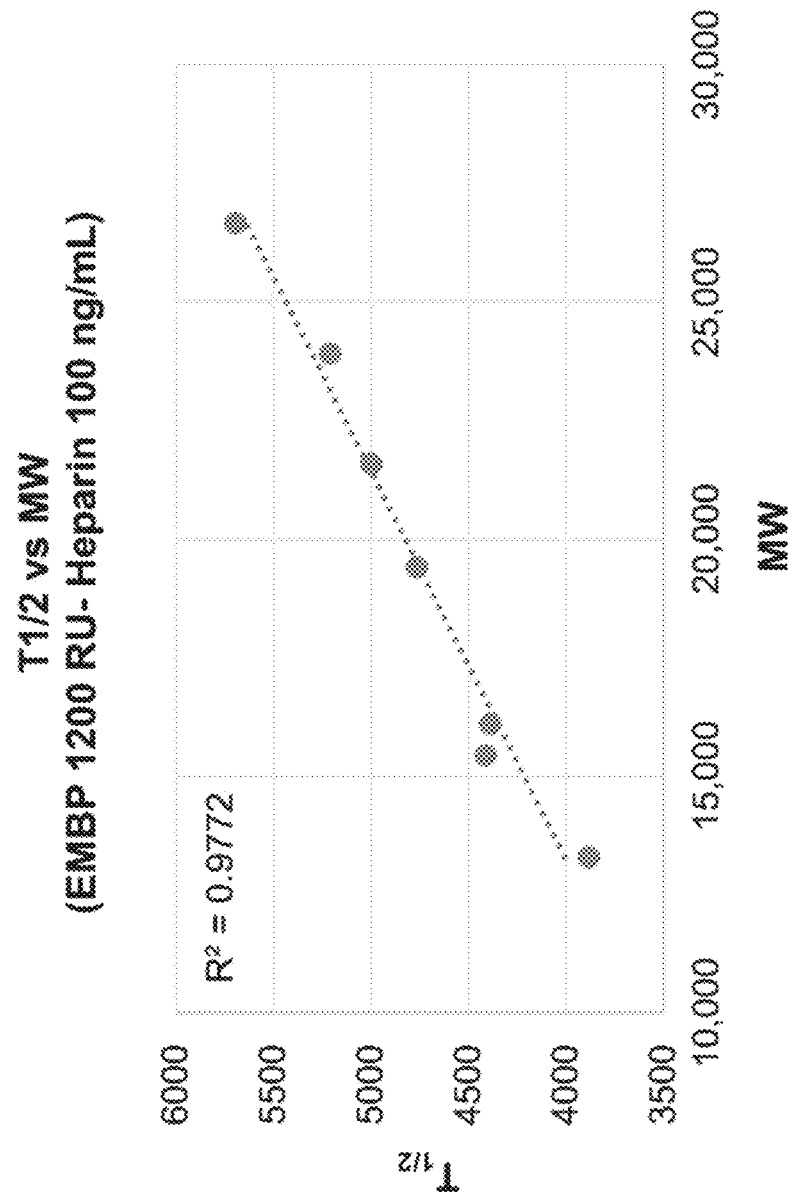
FIG. 3 depicts a plot graph of complex half-life versus molecular weight for seven heparin samples of varying molecular weights at a concentration of 100 ng/mL binding to eMBP1 at a density of 1200 RU in accordance with an embodiment.

Referring now to FIGS. 2A-2B, sensorgrams of the signal response for fractionated heparin samples (i.e., analytes) binding to rhu eMBP1 (i.e., ligand) are depicted in accordance with an embodiment. FIG. 2A depicts signal response curves over time for seven heparin samples of varying molecular weights at a concentration of 100 ng/mL binding to eMBP1 at a density of 1200 RU in accordance with an embodiment. FIG. 2B depicts normalized signal response curves over time for seven heparin samples of varying molecular weights at a concentration of 100 ng/mL binding to eMBP1 at a density of 1200 RU. Referring now to FIG. 3, a plot graph of complex half-life versus molecular weight is depicted for seven heparin samples of varying molecular weights at a concentration of 100 ng/mL binding to eMBP1 at a density of 1200 RU in accordance with an embodiment. FIGS. 2A-2B and 3 demonstrate a correlation between complex half-life and molecular weight of heparin as discussed herein.

Further, some assay conditions diverged from this correlation, which underscores the complexity of the multimeric and polydisperse heparin samples binding to eMBP1 surfaces. While a general correlation of higher binding response to higher molecular weight of heparin was observed, this response was not seen in all conditions including the most extreme avidity conditions. Under conditions that favor the greatest amount of avidity (i.e., high density of eMBP1 and low concentration of heparin), no apparent correlation was observed. This phenomenon may be explained by the fact that a greater number of subunits binding for each heparin molecule results in greater similarity of the complex half-life between the various molecular weight species, thereby reducing the dynamic range for the assay.

In addition, an apparent decay of signal response after each binding cycle was observed. Therefore, complex half-life is a better assessment tool for the assay as opposed to response signal.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of manufacturing fractionated heparin, the method comprising:
   dissolving heparin in a solvent to form a heparin solution;
   filtering the heparin solution through a submicron membrane to sterilize the heparin solution; and
   fractionating the filtered heparin solution by tangential flow filtration using a fractionation membrane with a molecular weight cut off between about 8 kDa and about 12 kDa, thereby yielding fractionated heparin with a weight average molecular weight of about 20 kDa or greater,
   wherein at least 50% of heparin chains in the fractionated heparin have a molecular weight of 20 kDa or greater.

2. The method of claim 1, wherein the heparin is USP heparin.

3. The method of claim 1, wherein the solvent is a sodium chloride (NaCl) solution.

4. The method of claim 3, where the NaCl solution has a concentration of about 100 mM.

5. The method of claim 1, wherein the molecular weight cut off of the fractionation membrane is about 10 kDa.

6. The method of claim 1, wherein fractionating the heparin solution by tangential flow filtration comprises permeating at least some of the heparin solution through the fractionation membrane under an applied pressure to yield a retentate comprising the fractionated heparin.

7. The method of claim 6, wherein the applied pressure is about 29 psi to about 30 psi.

8. The method of claim 6, wherein fractionating the heparin solution by tangential flow filtration further comprises adding an additional quantity of the solvent to maintain a volume of the retentate.

9. The method of claim 1, further comprising desalting the fractionated heparin.

10. The method of claim 9, wherein desalting the fractionated heparin comprises performing tangential flow filtration using a desalting membrane with a molecular weight cut off between about 1 kDa and about 5 kDa.

11. The method of claim 10, wherein the molecular weight cut off of the desalting membrane is about 3 kDa.

12. The method of claim 1, further comprising drying the fractionated heparin.

13. The method of claim 12, wherein drying the fractionated heparin comprising lyophilizing the fractionated heparin.

14. The method of claim 1, wherein the weight average molecular weight of the fractionated heparin is about 30 kDa or greater.

15. The method of claim 14, wherein the weight average molecular weight of the fractionated heparin is about 40 kDa or greater.

16. The method of claim 1, wherein the at least 60% of the heparin chains in the fractionated heparin have a molecular weight of 20 kDa or greater.

17. The method of claim 16, wherein the at least 70% of the heparin chains in the fractionated heparin have a molecular weight of 20 kDa or greater.

18. A method of manufacturing a high molecular weight (HMW) heparin, the method comprising:
   dissolving a heparin salt in a salt solution to form a heparin solution;

sterilizing the heparin solution by filtering through a sterilization membrane having a pore size of about 0.2 μm, thereby yielding a sterilized heparin solution;

fractionating the sterilized heparin solution by tangential flow filtration using a fractionation membrane with a pore size of about 5 nm, thereby yielding fractionated heparin with a weight average molecular weight of about 20 kDa or greater, wherein at least 50% of heparin chains in the fractionated heparin have a molecular weight of 20 kDa or greater;

desalting the fractionated heparin by tangential flow filtration using a desalting membrane with a pore size of about 3 nm, thereby yielding desalted heparin; and drying the desalted heparin by lyophilization to yield the HMW heparin.

19. The method of claim 18, wherein the heparin salt is selected from the group consisting of heparin sodium and heparin calcium.

20. The method of claim 18, wherein the heparin salt is a USP heparin salt.

21. The method of claim 18, wherein the salt solution is a sodium chloride (NaCl) solution.

22. The method of claim 21, where the NaCl solution has a concentration of about 100 mM.

23. The method of claim 18, wherein the molecular weight cut off of the fractionation membrane is about 10 kDa.

24. The method of claim 18, wherein fractionating the sterilized heparin solution by tangential flow filtration comprises permeating at least some of the sterilized heparin solution through the fractionation membrane under an applied pressure to yield a retentate comprising the fractionated heparin.

25. The method of claim 24, wherein the applied pressure is about 29 psi to about 30 psi.

26. The method of claim 24, wherein fractionating the sterilized heparin solution by tangential flow filtration further comprises adding an additional quantity of the salt solution to maintain a volume of the retentate.

27. The method of claim 18, wherein the molecular weight cut off of the desalting membrane is about 3 kDa.

28. The method of claim 18, wherein the weight average molecular weight of the fractionated heparin is about 30 kDa or greater.

29. The method of claim 28, wherein the weight average molecular weight of the fractionated heparin is about 40 kDa or greater.

30. The method of claim 18, wherein the at least 60% of the heparin chains in the fractionated heparin have a molecular weight of 20 kDa or greater.

31. The method of claim 30, wherein the at least 70% of the heparin chains in the fractionated heparin have a molecular weight of 20 kDa or greater.

32. The method of claim 18, wherein fractionating the sterilized heparin solution by tangential flow filtration comprises permeating at least some of the sterilized heparin solution through the fractionation membrane under a transmembrane pressure of about 30 psi such that (1) heparin chains in the sterilized heparin having a molecular weight of less than 20 kDa permeate through the filtration membrane as a filtrate, and (2) heparin chains in the sterilized heparin having a molecular weight of 20 kDa or greater do not permeate the filtration membrane, thereby yielding the retentate comprising the fractionated heparin, wherein the heparin salt comprises heparin sodium and the salt solution comprises sodium chloride (NaCl) solution in a concentration of about 100 mM.

* * * * *